United States Patent [19]

Hearon et al.

[11] 4,208,350

[45] Jun. 17, 1980

[54] SEPARATING PHENOLS FROM ALKALINE PULPING SPENT LIQUORS

[75] Inventors: William M. Hearon, Portland, Oreg.; Cheng F. Lo, Vancouver, Wash.

[73] Assignee: Boise Cascade Corporation, Boise, Id.

[21] Appl. No.: 883,413

[22] Filed: Mar. 6, 1978

[51] Int. Cl.² ............... C07C 37/36; C07C 45/24; C07C 41/12; C07C 37/38

[52] U.S. Cl. .................. 568/324; 568/653; 568/752; 568/762; 568/438

[58] Field of Search ............... 568/762, 761, 653, 752; 260/592, 600 A

[56] References Cited

U.S. PATENT DOCUMENTS

| | | | |
|---|---|---|---|
| 2,104,701 | 1/1938 | Sandborn | 260/137 |
| 2,489,200 | 11/1949 | Sanky et al. | 260/600 |
| 2,721,221 | 10/1955 | Bryon | 260/600 |
| 2,871,270 | 1/1959 | Alberda | 260/600 |
| 3,375,283 | 3/1968 | Goheen et al. | 260/613 |

FOREIGN PATENT DOCUMENTS 1014973 8/1977 Canada .................... 260/574

OTHER PUBLICATIONS

Chernovsov et al., Tr. Vies, Nauch–Issled Tsellyul–Bum Prom (1972), No. 61, pp. 172–180.
Browning, "Chemistry of Wood," Interscience Pub., pp. 464 and 481 (1963).

Primary Examiner—Werren B. Lone
Attorney, Agent, or Firm—Eugene D. Farley

[57] ABSTRACT

Phenol, ortho-cresol, meta- and para-cresols, guaiacol, vanillin, acetovanillone and other phenols are separated from alkaline pulping spent liquors by extracting the alkaline liquors with a lower aliphatic alcohol having from 2–5 carbon atoms inclusive, separating the solvent and aqueous phases, and thereafter separating the phenols from the solvent phase.

14 Claims, No Drawings

SEPARATING PHENOLS FROM ALKALINE PULPING SPENT LIQUORS

BACKGROUND AND SUMMARY OF THE INVENTION

This invention pertains to a process for separating phenols from spent aqueous liquors derived from the alkaline pulping of lignocellulose. It pertains particularly to a process for separating phenols from the alkaline black liquors derived from pulping wood by the kraft and soda processes.

As used herein, the term "phenols" is used in its generic sense and pertains not only to phenol itself, but also to phenolic-type compounds generally, and in particular to phenol, orthocresol, meta- and para-cresols, guaiacol, vanillin and acetovanillone.

With the exception of the last named, all of the foregoing phenols have known and important industrial uses. Phenol itself is widely used in plastics, plasticizers, resins, adhesives, fibers, medicinals, herbicides and biocides. The cresols are used in making herbicides, resins, plasticizers, disinfectants, antioxidants and in ore flotation. Guaiacol is used in medicinals and for making perfumes and flavoring materials. Vanillin is well known as a flavoring agent and is used in making medicines.

It is well known that during the alkaline pulping of lignocellulose, phenols of the class described above are produced in substantial quantities by the breakdown of the lignin content of the lignocellulose. For example, a typical sample of kraft black liquor contains 0.85% by weight on a solids basis of such materials. The spent aqueous liquors derived from the alkaline pulping of lignocellulose thus represent a potential source of enormous quantities of phenolic materials. A typical 1,000 tons a day kraft pulp mill, for example, produces from 1550 to 1900 tons of black liquor solids per day. The phenolic content of this quantity of black liquor solids is of the order of from 21,500 to 37,500 pounds.

Up to the present time, there has been no successful attempt to recover commercially the large quantities of phenolic compounds present in this source. These materials presently remain in the black liquor and are burned in the mill recovery cycle.

The reason for this waste of important industrial chemicals is that heretofore no practical, one-step method has been available for isolating them in the small percentage quantities in which they are present from the huge volumes of alkaline liquor in which they are contained.

U.S. Pat. Nos. 2,104,701, 2,489,200, 2,721,221 and 2,871,270 disclose procedures for producing vanillin from waste acid sulfite pulping liquor. However, these procedures require first neutralizing the liquor, which is on the acid side, to produce an alkaline liquor; then oxygenating the alkaline liquor to convert part of its lignosulfonic acid content to vanillin; and then separating the vanillin from the oxygenated liquor.

U.S. Pat. No. 3,375,283 discloses a process for the preparation of methoxyphenols from spent kraft pulping liquor, but by first drying the liquor to a solid and then pyrolizing the resulting solid at 300°–600° C. to generate the methoxyphenols which are separated from the pyrolysate by extraction with benzene.

Chernovsov et al Tr. Vies. Nauch.—Issled Iust. Tsellyul. — Bum. Prom. 1972, No. 61, pp. 172–80 (Chemical Abstracts, Vol. 80, p. 5089×(1974) ) disclose a procedure for isolating from kraft black liquor an extract one component of which is guaiacol. The process consists of: (1) acidifying the alkaline liquor with concentrated hydrochloric acid; (2) heating the liquor to 70° C.; (3) filtering to remove lignin; (4) saturating with sodium chloride; and (5) extracting with diethyl ether. However, the yield of guaiacol is poor and the guaiacol product is heavily contaminated by non-phenolic components from which it can only be extracted by a time-consuming and difficult supplemental procedure.

We now have discovered, and it is the essence of this invention, that the phenolic content of spent aqueous liquors derived from the alkaline pulping of lignocellulose may be separated from the liquors *without acidification* by the simple expedient of extracting them from the alkaline liquor with a solvent comprising essentially a lower aliphatic alcohol having from 2–5 carbon atoms inclusive, in particular with a propyl alcohol. When this is done, the alcohol solvent extracts the phenolic compounds in the form of their sodium salts, selectively and in high yield. This is accomplished without the necessity of subjecting the liquors to any chemical pretreatment preliminary to the extraction. In addition, it leaves the black liquor in a condition suitable for return to the recovery system of the pulp mill.

DESCRIPTION OF PREFERRED EMBODIMENTS OF THE INVENTION

Spent aqueous liquors suitable for use in the presently described process for separation of phenolic compounds broadly comprise those derived from the alkaline pulping of lignocellulose, particularly those derived from the alkaline pulping of either hardwood or softwood or mixtures thereof. Suitable liquors thus are those derived from the conventional kraft and soda processes as practiced throughout the world. Such liquors are alkaline, having a pH of at least 10. The usual pH of commercial kraft or soda spent pulping liquor is from about pH 11 to about pH 13.

In the kraft process, wood chips are cooked for from 2–4 hours at a temperature of 160° to 175° C. More specifically, they are cooked in a typical instance at 170° to 173° C. at a steam pressure of 100 to 110 psi. The cooking liquor comprises combined sodium hydroxide and sodium sulfide used in amounts of 40 to 50 grams per liter, calculated as $Na_2O$.

At the end of the cook the pulp and black liquor are blown into the blow tank where they are diluted with weak black liquor resulting from a prior run. The black liquor is separated from the pulp, the latter then being washed and applied to its intended use.

The procedure followed in the soda process is similar except that sodium sulfide is used in a relatively minor proportion, if at all. The principal cooking agent is sodium hydroxide. Cooking temperatures range from 160° to 180° and cooking times from 4 to 6 hours. The sodium hydroxide cooking agent is used in an amount of 50 to 60 grams per liter, calculated as $Na_2O$.

Both of these alkaline pulping procedures attack the lignin of the lignocellulose and convert it in part to phenol and its derivatives. The black liquor resulting from a typical softwood alkaline pulping procedure will contain about 0.85% by weight solids basis, of phenolic compounds. Typically, these will be distributed as follows:

|  | Percent by Weight |
| --- | --- |
| Phenol | 1.44 |
| Ortho-cresol | 6.92 |
| Meta- and para-cresols | 10.97 |
| Guaiacol | 32.18 |
| Vanillin | 28.28 |
| Acetovanillone | 13.92 |
| Other phenols | 6.28 |

To render the waste liquors susceptible to the herein-described procedure for separation of the phenols, it is only required, or at least desirable for practical reasons, to concentrate these liquors to a solids content of up to about 50% by weight, preferably from 25 to 45% by weight. This may be accomplished by the application of multiple-effect evaporators or other suitable concentrating equipment.

For separation of their content of phenolic compounds, the spent aqueous liquors are extracted with a selective solvent for such compounds. Such a solvent must meet the following criteria:

It must be a good solvent for phenolates, since the phenols are in the form of their alkali metal (sodium) salts.

It must not be substantially soluble in the waste liquor, so that a two-phase system may be established.

It should not react with the black liquor or with sodium phenolates.

It should remove the phenolates selectively from the spent liquors, a matter difficult of accomplishment in view of the highly diverse composition of the same.

It should not be too high boiling and should be readily removable from the extracted phenolates in a condition suitable for recycling and without introducing impurities into the phenolates.

It should be economically practical, i.e. available in large quantities at low cost.

It must be recoverable.

Its density should be such as to establish as high a density differential as possible between the solvent and black liquor phases.

It must establish as large an interfacial tension as possible between the solvent and black liquor phases.

Finally, the distribution coefficient for the sodium phenolates between the black liquor and solvent must be as high as possible.

Of all the commercially available organic solvents, we have found that one group of solvents meets the foregoing criteria best and is most suitable for the large scale commercial separation of phenolic compounds from spent aqueous pulping liquors. The solvents comprising this group are the low molecular weight aliphatic, alcohols, including ethanol, n-propanol, i-propanol, n-butanol, secondary butanol, isobutanol, tertiary butanol, and all of the pentanols. For the purposes of the present invention these alcoholic solvents may be used singly or in admixture with each other.

The extraction of the spent pulping liquor with the alcohol solvent is carried out using a suitable ratio of solvent to liquor, as determined by the source and composition of the liquor and the other operating conditions. In general, a ratio of 0.5–3 to 1, solvent to liquor, is suitable.

The extraction with solvent is carried out in any appropriate type of extraction equipment, operated in any desired number of stages, depending upon the distribution coefficient of the particular solvent mixture employed.

The temperature of extraction varies from just above the freezing temperature to about the boiling temperature of the solvent. Atmospheric pressure may be employed. Where atmospheric pressure is used, since the black liquor normally is processed hot from the mill, the temperature of extraction will vary between about 20° and about the boiling temperature of the solvent.

The extraction results in the formation of a solvent phase containing the phenols, and a raffinate, or residual black liquor phase. These are separated in conventional manner. The solvent phase then is treated for separation of its content of phenolic materials.

In one mode of operation the solvent phase is distilled to remove solvent and concentrate the extract. The concentrated extract is acidified with a slight excess of an acid such as sulphuric acid or phosphoric acid. This converts the sodium phenolates to the free phenols. The medium containing the free phenols is extracted with a suitable solvent such as toluene, after which the solvent is removed by evaporation. This leaves a residue of mixed phenols which may be separated by fractional distillation.

The black liquor from which the phenolic materials have been removed is steam stripped to remove any residual solvent and then returned to the spent liquor recovery system and processed in the usual way. The solvent removed by the steam stripping is combined with the solvent recovered by distillation from the solvent phase and recycled to the extractor for treatment of a further quantity of spent liquor.

The process of the invention is further illustrated by the following examples.

EXAMPLE 1

This example illustrates the application of the process of the invention to the extraction of phenols from kraft black liquor using isopropanol as a solvent.

Black liquor, 0.35 liter, resulting from the commercial kraft pulping of softwood chips was employed as a starting material. It had a solids content of 35.50% and a pH after soap skimming of 13.20. The liquor was extracted with azeotropic isopropanol containing 12.20% water at room temperature continuously for ten cycles, using 3500 ml. of azeotropic isopropanol (350 ml/cycle).

The isopropanol solvent in the light phase was removed by distillation at 79°–82° C. The resulting concentrated extract was diluted with 120 ml. of water to give a solution having a pH of 12.65. The solution was acidified with 29.00% sulphuric acid until its pH was 6.50.

The resulting black, heavy precipitate was removed by filtration and the filtrate was extracted three times with 50 ml. diethyl ether at room temperature. The combined ether extracts were evaporated in a rotary evaporator at 15°–25° C. to a minimum volume of about 5.0 ml.

The concentrate was then examined by gas chromatography for phenolic compounds, using Hewlett Packard Model 700 gas chromatography, 12 feet 10% SE 30′ ⅛″ stainless steel column at 140° C. with 20 ml. per minute helium.

The results of the analysis are given in Table I below:

Table I

| COMPOUNDS | PHENOLS CONTENT BASED ON 40% BLACK LIQUOR (grams/gallon) (Converted from 35.50% values for purposes of comparison) |
|---|---|
| Phenol | 0.169 |
| o-Cresol | 0.391 |
| m-, p-Cresols | 1.508 |
| Guaiacol | 4.132 |
| Xylenols | 0.938 |
| Vanillin | 6.470 |
| Acetovanillone | 4.855 |
| Other Phenols | 0.556 |

EXAMPLE 2

This example illustrates the application of the process of the invention to the extraction of phenolic compounds from soda black liquor using isopropanol as the solvent.

The procedure of Example 1 was followed, but using 35.0% solids soda liquor as the starting material. The results of the analysis are shown in Table II below.

Table II

| | GRAMS/GALLON OF 40% BLACK LIQUOR |
|---|---|
| Phenol | 0.131 |
| o-Cresol | 0.483 |
| m-, p-Cresols | 1.590 |
| Guaiacol | 4.971 |
| Xylenols | 0.583 |
| Other Phenols | 1.011 |
| Vanillin | 6.257 |
| Acetovanillone | 4.591 |

EXAMPLE 3

This example illustrates the application of the process of the invention to the extraction of phenolic compounds from kraft cooking waste liquor using n-propanol as the extracting solvent.

Six hundreds milliliters of commercial softwood kraft black liquor having a pH of about 12.5 and containing 37.50% solids was extracted continuously in a 1.5 inch by 4.0 foot glass column with azeotropic n-propanol containing 28.2% water. The extraction temperature was 60° C. 6.50 Cycles of extraction were employed using 600 ml. azeotropic n-propanol.

The organic phase resulting from the extraction was separated and evaporated to a thick syrup followed by acidification with 10.00 ml. glacial acetic acid to a pH of 7.00.

The neutralized extract containing the free phenols was extracted with three 50 ml. portions of diethyl ether. The combined ether extracts were concentrated to about 20 ml. under vacuum at room temperature.

The resulting ether concentrate was examined by gas chromatography. The results are shown in the following table.

Table III

| COMPOUNDS | GRAMS/GALLON OF 40% BLACK LIQUOR |
|---|---|
| Phenol | 0.181 |
| o-Cresol | 0.462 |
| m-, p-Cresols | 1.592 |
| Guaiacol | 5.270 |
| Xylenols | 0.761 |
| Other Phenols | 1.010 |
| Vanillin | 6.939 |
| Acetovanillone | 4.224 |

EXAMPLE 4

This example illustrates the application of the process of the invention to the extraction of phenolic compounds from black liquor using n-butanol as the solvent.

4.00 Liters of commercial softwood kraft black liquor having a solids content of 32.33% and a pH of 13.15 was extracted continuously for 48 hours in a 125 cm. by 8.20 cm. glass column with azeotropic n-butanol containing 20.1% water. At the end of the extraction the organic solvent phase was separated and distilled until most of the butanol had been removed.

The resulting deep brown concentrate was dissolved in 200 ml. of water and acidified to a pH of 6.50 with 50% sulfuric acid to spring the phenols. The acidified mixture was extracted with three 100 ml. portions of diethyl ether. The combined ether extracts were concentrated and the concentrate examined by gas chromatography.

The analysis showed that the extract contained 4.0137 grams of guaiacol and 0.1432 grams phenol per gallon of black liquor starting material. The amounts of o-cresol, m- and p-cresols, vanillin and acetovanillone were substantially the same as given in Example 2 on the same black liquor concentration basis.

EXAMPLE 5

This example illustrates the distribution coefficient of guaiacol and vanillin in the solvent phase resulting from a single extraction of phenolic compounds from kraft black liquor by the herein described process, using various organic solvents at two different temperatures: 25° C. and 65° C.

Kraft black liquor, 100 ml., was vigorously shaken with 100 ml. of an azeotropic organic solvent in a 250 ml. graduated cylinder. The time required for maximum phase separation and its volume were recorded.

The organic solvent phase was worked up as in Example 1; i.e. the organic solvent was distilled off, the phenolic compounds extracted from the neutralized residue (pH - 6.50) with an equal volume of diethyl ether three times. The concentrated ether extracts were then examined by the chromatograph. The yields of guaiacol and vanillin from the single extraction and their distribution coefficients are shown in the following tables.

TABLE IV - A

| | SOLVENTS | | | | | | |
|---|---|---|---|---|---|---|---|
| | EtOH | n-propanol | i-propanol | n-BuOH | 2-BuOH | i-BuOH | t-BuOH |
| CONDITIONS | | | | | | | |
| Black Liquor solid % by weight | 49.50 | 49.50 | 49.50 | 39.50 | 39.50 | 39.50 | 39.50 |
| Extraction Temperature °C. | 25 | 25 | 25 | 25 | 25 | 25 | 25 |
| Time for Complete Phases Separation (Minutes) | 10 | 10 | 6 | 6 | 15 | 15 | 10 |
| Maximum Volume of Organic Phase (ml) | 110 | 86 | 105 | 101 | 93 | 96 | 105 |

TABLE IV - A-continued

| | SOLVENTS | | | | | | |
|---|---|---|---|---|---|---|---|
| | EtOH | n-propanol | i-propanol | n-BuOH | 2-BuOH | i-BuOH | t-BuOH |
| Solid in Organic Phase (Grams) | 15.50 | 6.46 | 2.57 | 2.00 | 0.85 | 0.70 | 0.80 |
| EXTRACTED MATERIAL | | | | | | | |
| Guaiacol (grams/gallon) | 2.960 | 2.468 | 2.178 | 1.669 | 0.638 | 0.520 | 0.866 |
| | (6.180) | (6.180) | (6.180) | (4.295) | (4.295) | (4.295) | (4.295) |
| Vanillin (grams/gallon) | 2.928 | 4.104 | 3.812 | 1.589 | 0.974 | 0.775 | 1.583 |
| | (5.992) | (5.992) | (5.992) | (5.406) | (5.406) | (5.406) | (5.406) |
| Distribution Coefficient | | | | | | | |
| Guaiacol | 0.921 | 0.660 | 0.540 | 0.637 | 0.174 | 0.138 | 0.202 |
| Vanillin | 0.960 | 2.170 | 1.750 | 0.416 | 0.220 | 0.167 | 0.414 |

Note:
Parentheses denote the amount of guaiacol and vanillin contained in unextracted liquor.

TABLE IV - B

| | SOLVENTS | | | | | | |
|---|---|---|---|---|---|---|---|
| | EtOH | n-propanol | i-propanol | n-BuOH | 2-BuOH | i-BuOH | t-BuOH |
| CONDITIONS | | | | | | | |
| Black liquor solid % by weight | 39.50 | 39.50 | 39.50 | 39.50 | 39.50 | 39.50 | 39.50 |
| Extraction Temperature °C. | 65 | 65 | 65 | 65 | 65 | 65 | 65 |
| Time for Complete Phases Separation (Minutes) | 45 | 45 | 45 | 10 | 10 | 6 | 10 |
| Maximum Volume of Organic Phase (ml) | 102 | 107 | 101 | 93 | 106 | 102 | 102 |
| Solid in Organic Phase (g) | 10.08 | 9.76 | 2.34 | 1.10 | 0.90 | 0.85 | 0.84 |
| EXTRACTED MATERIAL | | | | | | | |
| Guaiacol (g/gallon) | 1.751 | 1.980 | 1.720 | 1.300 | 0.730 | 0.720 | 0.555 |
| | (4.297) | (4.980) | (4.980) | (4.980) | (4.980) | (4.980) | (4.980) |
| Vanillin (g/gallon) | 2.591 | 3.360 | 3.220 | 2.000 | 1.340 | 1.580 | 1.100 |
| | (5.407) | (4.960) | (4.960) | (4.960) | (4.960) | (4.960) | (4.960) |
| Distribution Coefficient | | | | | | | |
| Guaiacol | 0.69 | 0.66 | 0.52 | 0.35 | 0.24 | 0.21 | 0.12 |
| Vanillin | 0.92 | 2.10 | 1.85 | 0.68 | 0.36 | 0.46 | 0.28 |

Note:
Parentheses denote the amounts of guaiacol and vanillin contained in unextracted black liquor.

EXAMPLE 6

This example illustrates the application of the invention to the extraction of phenolic compounds from a hardwood black liquor.

Black liquor, 0.35 liter, resulting from the laboratory kraft pulping of red alder chips (Alnus rubra) was employed as a starting material. It had a solid content of 38.63% and a pH of 13.10. The liquor was extracted with azeotropic isopropanol containing 12.20% water at room temperature continuously for ten cycles using 3500 ml. of azeotropic isopropanol (350 ml/cycle).

The isopropanol solvent in the light phase was removed by distillation at 79°-82° C. The resulting concentrated extract wasdiluted with 120 ml. of water and was acidified with 20% $H_2SO_4$ to pH 6.50. The resulting black, heavy precipitate was removed by filtration and the filtrate was extracted with three portions of 50 ml. diethyl ether. The combined ether extracts were evaporated under rotary evaporators at room temperature to about 5.0 ml.

The phenolic content in the concentrated extract was examined by gas chromatography as described in Example 1.

The results of the analysis are given in Table V below.

Table V

| COMPOUNDS | PHENOLIC CONTENT BASED ON 40% BLACK LIQUOR (G/GALLON) |
|---|---|
| Phenol | 0.027 |
| o-Cresol | 0.054 |
| m-, p-Cresols | 0.117 |
| Guaiacol | 0.470 |
| Xylenols | 0.116 |
| Other Phenols | 0.225 |
| Vanillin | 1.252 |
| Acetovanillone | 0.973 |
| Acetosyringone | 0.437 |

EXAMPLE 7

This example illustrates the application of the invention to the extraction of phenolic compounds from black liquor using pentanol as a solvent.

Black liquor, 0.35 liter, resulting from the commercial kraft pulping of softwood chips was employed as a starting material. It had a solid content of 35.50% and a pH of 13.20. The liquor was extracted with azeotropic 2-pentanol (67.80% by weight) at room temperature for 16.00 hours.

The solvent, 2-pentanol, in the light phase was removed by distillation and the concentrated extract was worked up as in Example 1. The phenolic compounds in the extract were examined by a gas chromatograph as it is described in Example 1.

The results of the analyses are given in Table VI.

TABLE VI

| PHENOLIC COMPOUNDS | PHENOLS, GRAMS/GALLON 40% BLACK LIQUOR | |
|---|---|---|
| | Amount Extracted | Amount Present |
| Phenol | 0.153 | (0.169) |
| o-Cresol | 0.283 | (0.391) |
| m-, p-Cresols | 0.908 | (1.508) |

TABLE VI-continued

| PHENOLIC COMPOUNDS | PHENOLS, GRAMS/GALLON 40% BLACK LIQUOR | |
|---|---|---|
| | Amount Extracted | Amount Present |
| Guaiacol | 3.908 | (4.132) |
| Xylenols | 0.717 | (0.938) |
| Other Phenols | 0.347 | (0.372) |
| Vanillin | 4.054 | (6.470) |
| Acetovanillone | 2.067 | (4.855) |

Note: Parentheses denote the amounts of phenols in unextracted black liquor.

EXAMPLE 8

This example illustrates a manner of separation of vanillin from other phenolic compounds of the phenolic extract produced by the process of the invention.

A neutral ether soluble phenolic extract, 65 ml., obtained from isopropanol exhaustive extraction 3 liters of 35.50% softwood black liquor was used as the starting material. The solution contained 4.00 grams vanillin and 8.463 grams of other phenolic compounds (see Table VII). The solution was mixed with 4.105 grams NaHSO$_3$ in 100 ml. water with continuous stirring for three hours at room temperature at pH 2.50. The pH was controlled by adding 5.50% sulphurous acid. After stirring, the oily light phase was removed by extraction with three portions of 100 ml. diethyl ether.

The light brown raffinate was concentrated to 50 ml. at 60° C. under vacuum to remove excess sulfur dioxide. The concentrate was neutralized with dilute sodium hydroxide to pH 6.50 and was extracted with three portions of 60 ml. diethyl ether. The combined ether extracts were evaporated to dryness giving a dry weight of 3.876 grams (96.90% recovered) of vanillin. The product had a melting point of 78°–80° C. and was not depressed by an authentic sample of vanillin. The crude product showed only one peak (corresponding to vanillin) in the gas chromatogram. Gas chromatographic examination of the oily light phase after vanillin removal showed that the other phenols had not been removed by the bisulfite treatment.

Table VII

| COMPOUNDS | BEFORE EXTRACTION | AFTER EXTRACTION |
|---|---|---|
| Phenol | 0.104 | 0.101 |
| o-Cresol | 0.262 | 0.254 |
| m-, p-Cresols | 0.907 | 0.902 |
| Guaiacol | 3.476 | 3.453 |
| Xylenols | 0.582 | 0.573 |
| Other Phenols | 0.441 | 0.431 |
| Vanillin | 4.000 | 0.170 |
| Acetovanillone | 2.753 | 2.749 |

EXAMPLE 9

Separation of phenols by fractional distillation using tall oil as a heel oil.

A mixture of 54 grams of phenolic compounds and 100 ml. of tall oil in a 350 ml. round bottle flask was fractionally distilled using a 1.5×37 cm. glass column at atmospheric pressure. The column was packed with 4.5 mm. (I.D.) glass helices and was insulated with 2" thick of glass wool. The mixture of phenolic compounds consisted of: phenol, 3.00 g; o-cresol, 6.50 g; m,p-cresols, 5.00 g; (1.0 to 1.0 ratio); guaiacol 32.50 g; and 3,5 xylenol 7 00 g.

Fractions of the distillate were collected based on the boiling point ranges of each individual compound. The composition of each fraction was determined by the gas chromatographic method as it is described in Example 1. The results are given in Table VIII.

TABLE 8

| Fractions NO <1 | Temperature °C. | Weight (g) | Phenol % | g | O-cresol % | g | m,p-cresol % | g | Guaiacol % | g | Xylenol % | g |
|---|---|---|---|---|---|---|---|---|---|---|---|---|
| 1 | 170–177 | 2.1200 | 100 | 2.1200 | Trace | | Trace | | | | | |
| 2 | 186–195 | 5.0524 | 2.47 | 0.1248 | 88.49 | 4.4676 | 6.19 | 0.3127 | 2.91 | 0.1470 | Trace | |
| 3 | 196–200 | 0.9311 | 0.31 | 0.0029 | 68.25 | 0.6354 | 11.64 | 0.1084 | 19.80 | 0.1843 | Trace | |
| 4 | 200–202 | 7.4210 | 0.80 | 0.0593 | 15.94 | 1.1829 | 27.89 | 2.0697 | 55.37 | 4.1090 | Trace | |
| 5 | 202–204 | 8.3434 | 0.48 | 0.0400 | 2.61 | 0.0220 | 11.98 | 0.9995 | 84.97 | 7.0890 | Trace | |
| 6 | 204–205 | 14.7021 | Trace | | 0.32 | 0.0470 | 5.09 | 0.7084 | 94.63 | 13.9126 | 0.64 | 0.09 |
| 7 | 205–207 | 7.6504 | Trace | | Trace | | 1.84 | 0.1408 | 96.94 | 7.4160 | 1.22 | 0.09 |
| 8 <2 | 210–230 | 6.9851 | Trace | | Trace | | 2.05 | 0.1432 | 2.05 | 0.1432 | 95.90 | 6.69 |
| | SUBTOTAL | 53.2052 | | 2.3470 | | 6.3549 | | 4.4827 | | 33,0015 | | 6.88 |

NOTE:
There were no clear cut separations of each pure compound. However, the results showed they are separable by careful fractionation.
2 Part of the residual xylenol was distilled off under reduced pressure (water pump) at 130° C.

EXAMPLE 10

This example illustrates the unsuitability of various classes of solvents other than the lower alcohols for the purposes of the present invention.

The examples of commonly available solvents used are given below:

Hydrocarbons—cyclohexane, toluene

Halogenated hydrocarbons—chloroform, 1, 1.1—trichlorethane

Ethers—petroleum ether (B.P. 30–60° C.), diethyl ether, tetrahydrofurane and dioxane (1,4 diethylene oxide).

Ketone—4-methyl-2-pentanone

Black liquor, 0.35 liter, resulting from the commercial kraft pulping of softwood chips was employed as the starting material. The black liquor was extracted continuously with each individual solvent for 16.00 hours at room temperature. The work ups followed the procedure described in Example 1. The amounts of phenols extracted by each solvent are given in Table IX.

TABLE IX

| COMPOUNDS | EXTRACTED PHENOLS, GRAMS/GALLON 40% BLACK LIQUOR | | | | | | | | | |
|---|---|---|---|---|---|---|---|---|---|---|
| | Iso-propanol | Cyclo-hexane | Toluene | CHCl₃ | 1, 1.1-Tri Chloroethane | Pet. Ether | Ethyl Ether | Tetrahydro-furane | Dioxane | 4-ME-2 Pentanone |
| Phenol | 0.169 | Trace | 0.004 | 0.039 | Trace | 0.015 | 0.018 | 0.017 | 0.043 | 0.095 |
| o-cresol | 0.391 | Trace | 0.001 | | 0.002 | 0.010 | 0.016 | 0.006 | 0.001 | 0.005 |
| m,p-cresols | 1.508 | Trace | 0.014 | 0.138 | 0.006 | 0.006 | 0.003 | 0.053 | 0.012 | 0.029 |
| guaiacol | 4.132 | 0.072 | 0.394 | 0.570 | 0.721 | 0.099 | 0.553 | 0.208 | 0.097 | 2.336 |
| xylenols | 0.938 | Trace | 0.073 | 0.114 | 0.107 | 0.009 | 0.028 | 0.001 | — | 0.024 |
| other phenols | 0.372 | 0.019 | 0.008 | 0.039 | 0.068 | — | — | — | — | — |
| vanillin | 6.470 | 0.033 | 0.119 | 0.259 | 0.216 | 0.001 | 0.010 | 1.214 | — | 0.070 |
| acetovanillin | 4.885 | Trace | Trace | 0.151 | 0.137 | 0.003 | — | 0.694 | — | 0.426 |
| Total Extracted Phenols | 18.634 | 0.124 | 0.613 | 1.310 | 1.257 | 0.143 | 0.628 | 2.199 | 0.153 | 2.885 |
| Percent Extracted | 100.00 | 0.66 | 3.29 | 7.03 | 6.75 | 0.77 | 3.37 | 11.80 | 0.82 | 15.48 |

Having thus described our invention in preferred embodiments, we claim:

1. The process for the manufacture of phenols which comprises:
   (a) pulping lignocellulose by an alkaline pulping process to produce a cellulosic pulp product and an alkaline spent liquor containing a mixture of phenols as their alkali metal salts, the said phenols comprising phenol, cresol, xylenol, guaiacol, acetovanillone and vanillin,
   (b) separating the spent liquor from the pulp,
   (c) concentrating the spent liquor to a solids content of up to about 50% by weight,
   (d) extracting the concentrated spent liquor with a solvent comprising essentially a lower aliphatic alcohol having from 2-5 carbon atoms inclusive, at a temperature of from just above the freezing temperature to about the boiling temperature of the solvent, thereby forming a solvent phase containing the alkali metal salts of the phenols, and an aqueous phase,
   (e) separating the solvent phase from the aqueous phase,
   (f) concentrating the separated solvent phase by the removal of solvent therefrom,
   (g) acidifying, with an acid of the group consisting of sulfuric acid, phosphoric acid and acetic acid, the resulting concentrated solvent phase to convert the alkali metal salts of the phenols contained therein to free phenols,
   (h) solvent extracting the acidified and concentrated solvent phase with a substantially water immiscible selective solvent for free phenols,
   (i) separating the resulting free phenols solvent extract, and
   (j) fractionally distilling the free phenols solvent extract for separation of the phenols contained therein.

2. The process of claim 1 wherein the lignocellulose is pulped by the kraft process.

3. The process of claim 1 wherein the lignocellulose is pulped by the soda process.

4. The process of claim 1 wherein the spent liquor is concentrated to a solids content of from about 25% to about 45% by weight.

5. The process of claim 1 wherein the spent liquor has a pH of at least about 10.

6. The process of claim 1 wherein the solvent for the spent liquor comprises essentially ethanol.

7. The process of claim 1 wherein the solvent for the spent liquor comprises n-propanol.

8. The process of claim 1 wherein the solvent for the spent liquor comprises isopropanol.

9. The process of claim 1 wherein the solvent for the spent liquor comprises a butanol.

10. The process of claim 1 wherein the spent liquor is extracted with solvent at atmospheric pressure and at a temperature of between about 20° C. and about the boiling point of the solvent.

11. The process of claim 1 wherein the selective solvent for phenols comprises toluene.

12. The process of claim 1 including the step of adding tall oil to the crude mixture of phenols preliminary to fractional distillation thereof.

13. The process of claim 1 wherein the acid comprises sulfuric acid.

14. The process for the manufacture of phenols which comprises:
   (a) pulping lignocellulose by an alkaline peping process to produce a cellulosic pump product and an alkaline spent liquor having a pH of at least about 10 and containing a mixture of phenols as the alkali metal salts, the said phenols comprising phenol, cresol, xylenol, guaiacol, acetovanillone and vanillin,
   (b) separating the spent liquor from the pulp,
   (c) concentrating the spent liquor to a solids content of from about 20% to about 45% by weight,
   (d) extracting the concentrated liquor with a lower aliphatic alcohol having from 2-5 carbon atoms inclusive at substantially atmospheric pressure and at a temperature of between about 20° C. and about the boiling point of the alcohol solvent, thereby forming a solvent phase containing the alkali metal salts of the phenols and an aqueous phase,
   (e) separating the solvent phase from the aqueous phase,
   (f) distilling the alcohol solvent from the separated solvent phase,
   (g) acidifying with sulfuric acid the resulting residue to convert the alkali metal salts of the phenols contained therein to free phenols,
   (h) solvent extracting the acidified residue with a substantially water immiscible selective solvent for free phenols,
   (i) separating the resulting solvent phase contianing the free phenols from the resulting acid phase, and
   (j) fractionally distilling the solvent phase containing the free phenols for separation thereof into its component phenol products.

* * * * *